US011478191B1

(12) United States Patent
Roveda et al.

(10) Patent No.: US 11,478,191 B1
(45) Date of Patent: Oct. 25, 2022

(54) SMART MASK FOR COVID-19 SCREENING, TRACKING AND MONITORING

(71) Applicant: ESATTO HEALTHCARE, INC., Tucson, AZ (US)

(72) Inventors: Roberto Roveda, Tucson, AZ (US); Bijan Najafi, Houston, TX (US); Ryan G. Redford, Irvine, CA (US)

(*) Notice: Subject to any disclaimer, the term of this patent is extended or adjusted under 35 U.S.C. 154(b) by 0 days.

(21) Appl. No.: 17/221,765

(22) Filed: Apr. 2, 2021

Related U.S. Application Data

(60) Provisional application No. 63/005,150, filed on Apr. 3, 2020.

(51) Int. Cl.
| | |
|---|---|
| *A61B 5/00* | (2006.01) |
| *H04M 1/72412* | (2021.01) |
| *H04W 4/38* | (2018.01) |
| *H04W 4/029* | (2018.01) |
| *G16H 50/30* | (2018.01) |
| *G16H 40/67* | (2018.01) |

(Continued)

(52) U.S. Cl.
CPC ............ *A61B 5/6803* (2013.01); *A41D 13/11* (2013.01); *A61B 5/002* (2013.01); *A61B 5/01* (2013.01); *A61B 5/087* (2013.01); *A61B 5/0816* (2013.01); *A61B 5/0833* (2013.01); *A61B 5/0836* (2013.01); *A61B 5/486* (2013.01); *A61B 5/7465* (2013.01); *A61B 7/003* (2013.01); *G16H 40/67* (2018.01); *G16H 50/30* (2018.01); *H04M 1/72412* (2021.01); *H04M 1/72421* (2021.01); *H04W 4/029* (2018.02); *H04W 4/38* (2018.02); *A61B 5/0077* (2013.01); *A61B 5/1112* (2013.01); *A61B 5/14551* (2013.01); *G06V 40/28* (2022.01)

(58) Field of Classification Search
CPC ....... A61B 5/6803; A61B 5/087; A61B 5/002; A61B 5/0816; A61B 5/486; A61B 5/0836; A61B 5/01; A61B 5/7465; A61B 5/0833; A61B 7/003; A61B 5/0077; A61B 5/1112; A61B 5/14551; G16H 50/30; H04W 4/029; H04W 4/38; H04M 1/72421; H04M 1/72412; A41D 13/11; G06K 9/00355

See application file for complete search history.

(56) References Cited

U.S. PATENT DOCUMENTS

| 5,511,541 A | * | 4/1996 | Dearstine | ............... A62B 9/003 128/201.13 |
|---|---|---|---|---|
| 2008/0110469 A1 | * | 5/2008 | Weinberg | ........... A41D 13/1176 128/863 |

(Continued)

FOREIGN PATENT DOCUMENTS

| CN | 105231523 A | * | 1/2016 | ............. A41D 13/11 |
|---|---|---|---|---|
| KR | 101815757 B1 | * | 1/2018 | ............. A62B 18/02 |
| WO | WO-2015166444 A1 | * | 11/2015 | ............. A61B 5/097 |

OTHER PUBLICATIONS

Bai, Yu, et al. "Washable multilayer triboelectric air filter for efficient particulate matter PM2. 5 removal." Advanced Functional Materials 28.15 (2018): 1706680 (Year: 2018).*

(Continued)

*Primary Examiner* — Andrey Shostak
(74) *Attorney, Agent, or Firm* — Hayes Soloway P.C.

(57) ABSTRACT

A smart face mask comprising a mask body; a temperature sensor; a respiration sensor; and a transmitter for transmitting information from the temperature sensor, the respiration sensor and a geotracker to a smart phone or smart watch.

19 Claims, 5 Drawing Sheets

(51) Int. Cl.
*A61B 5/01* (2006.01)
*A61B 5/087* (2006.01)
*A41D 13/11* (2006.01)
*A61B 5/08* (2006.01)
*A61B 7/00* (2006.01)
*A61B 5/083* (2006.01)
*H04M 1/72421* (2021.01)
*A61B 5/11* (2006.01)
*A61B 5/1455* (2006.01)
*G06V 40/20* (2022.01)

(56) References Cited

U.S. PATENT DOCUMENTS

| | | | | |
|---|---|---|---|---|
| 2016/0315561 | A1* | 10/2016 | Shin | H02N 1/04 |
| 2017/0106217 | A1* | 4/2017 | Kuhn | A41D 13/1161 |
| 2018/0078798 | A1* | 3/2018 | Fabian | A62B 7/10 |
| 2019/0133496 | A1* | 5/2019 | Wood | G16H 50/30 |
| 2019/0142677 | A1* | 5/2019 | Linder | A61N 7/00 601/18 |
| 2019/0180594 | A1* | 6/2019 | Williams | G08B 21/12 |
| 2019/0314746 | A1* | 10/2019 | Leung | D01D 5/0084 |

OTHER PUBLICATIONS

English-language machine translation of CN-105231523-A (Year: 2022).*

English-language machine translation of KR-101815757-B1 (Year: 2022).*

Robero Roveda, Ph.D Thesis, a combined discrete velocity particle based numerical approach for continuum/rarefied flows, Sep. 2000; 14 pages.

Roberto Roveda, David Goldstein, Philip Leslie Varghese, Hybrid Euler/Direct Simulation Monte Carlo Calculation of Unsteady Slit Flow, Nov. 2000, Journal of Spacecraft and Rockets 37(6):753-760 DOI: 10.2514/2.3647; 8 pages.

Talib Dbouk, and Dimitris Drikakis, On respiratory droplets and face masks, Physics of Fluids 32, 063303 (2020); https://doi.org/10.1063/5.0015044' 12 pages.

G.-X. Xiong, J.-M. Zhan, K.-J. Zuo, L.-W. Rong, J.-F. Li, G. Xu, Use of computational fluid dynamics to study the influence of the uncinate process on nasal airflow., J. Laryngol. Otol. 125 (2011) 30-7. doi:10.1017/S002221511000191X.; 30 pages.

G. Xiong, J.-M. Zhan, H.-Y. Jiang, J.-F. Li, L.-W. Rong, G. Xu, Computational fluid dynamics simulation of airflow in the normal nasal cavity and paranasal sinuses, Am. J. Rhinol. 22 (2008) 477-482. doi:10.1007/s13398-014-0173-7.2.; 6 pages.

Aaditya Ruiker, Designing effective ventilation strategy for an Airborne infection isolation room (AIIR) using CFD, https://www.simulationhub.com/blog/designing-effective-ventilation-strategy-for-isolation-rooms-using-cfd, Jul. 2020; 14 pages.

A. Vie, H. Pouransari, R. Zamansky, and A. Mani, Comparison between Lagrangian and Eulerian methods for the simulation of particle-laden flows subject to radiative heating, Annual Research Briefs, 2014, Center for Turbulence Research; 13 pages.

Apte, S. V., Mahesh, K., Moin, P. & Oefelein, J. C. 2003 Large-eddy simulation of swirling particle-laden flows in a coaxial jet combustor. Int. J. Multiphase Flow 29, 1311-1331; 21 pages.

Choi, Y. H. & Merkle, C. L. 1993 the application of preconditioning in viscous flows. J. Comput. Phys. 105, 207-230' 1993; 17 pages.

Guillard, H. & Viozat, C. 1998 on the behaviour of upwind schemes in the low mach number limit. Comput. Fluids 28, 63-86; 1999; 24 pages.

I. B. Celik, U. Ghia, P. J. Roache, and C. J. Freitas, "Procedure for estimation and reporting of uncertainty due to discretization in CFD applications," J. Fluids Eng. 130, 078001 (2008). https://doi.org/10.1115/1.2960953; 4 pages.

H. A. Carlson, R. Roveda, Iain Boyd, Graham Candler, a hybrid CFD-DSMC method of modeling continuum-rarefied flows, Jan. 2004 DOI: 10.2514/6.2004-1180 Conference: 42nd AIAA Aerospace Sciences Meeting and Exhibit; 8 pages.

Roberto Roveda, David Goldstein, Philip Leslie Varghese, A combined discrete velocity/particle based numerical approach for continuum/rarefied flows, Jan. 1997 DOI: 10.2514/6.1997-1006, Conference: 35th Aerospace Sciences Meeting and Exhibit; 14 pages.

H. A. Carlson, M. N. Glauser, R. Roveda, Models for Controlling Airfoil Lift and Drag Jan. 2004 DOI: 10.2514/6.2004-579 Conference: 42nd AIAA Aerospace Sciences Meeting and Exhibit; 12 pages.

Roberto Roveda, David Goldstein, Philip Leslie Vaarghese, Hybrid Euler/Particle Approach for Continuum/Rarefied Flows May 1998Journal of Spacecraft and Rockets 35(3):258-265 DOI: 10.2514/2.3349; 8 pages.

Roberto Roveda, David Goldstein, Philip Leslie Vaarghese, Unsteady calculation of slit flow with 2-D hybrid Euler/DSMC numerical approach, Jan. 1998, DOI: 10.2514/6.1998-852, Conference: 36th AIAA Aerospace Sciences Meeting and Exhibit; 11 pages.

* cited by examiner

Fig. 5

(Left) Two layer copper mesh (brown) outside the regular face masks act as capacitor that provide charges against aerosol and COVID-19 virus with negative charges. (Middle) A simple self-activated no battery need triboelectric generator. (Right) Copper mesh material fabricated

Fig. 6

Hybrid method with Euler based CFD simulation for a room setting and then passes boundary conditions to Lagrangian Particle Simulation. Air pressure and velocity sensors on the wearable provide measurement data to Lagrangian simulations.

SMART MASK FOR COVID-19 SCREENING, TRACKING AND MONITORING

CROSS REFERENCE TO RELATED APPLICATION

This application claims priority from U.S. Provisional Application Ser. No. 63/005,150, filed Apr. 3, 2020, the contents of which are incorporated herein by reference.

BACKGROUND OF THE DISCLOSURE

The present disclosure relates to face masks and more particularly to smart face masks to help triage the sick and those exposed to high risk of infection. The disclosure has particular utility in connection with addressing the current Coronavirus or COVID-19 pandemic and will be described in connection with such utility, although other utilities are contemplated.

SUMMARY OF THE DISCLOSURE

The COVID-19 pandemic has infected hundreds of thousands of people worldwide with thousands of causalities. Today, the US has thousands of infected people with a growing number of causalities. The growing threat of the COVID-19 pandemic requires rapid actions to help triage the sick and keep the worried well out of already crowed medical facilities.

To address this challenge, we have designed a telehealth platform consisting of 1) a smart wearable in the form of a face mask or as an add-on to a conventional face mask having sensors which enable monitoring key symptoms and factors associated with COVID-19 including body temperature, dry coughing, frequency of coughing, fever, nausea, and shortage of breath; 2) a HIPAA compliant patient portal for sharing data with qualified care providers; 3) an app with geo-tracking feature to track locations and timing where the user stayed over time; 4) a smart search-engine to capture geographical location or zip codes, where infected people were diagnosed; 5) a smart alert device to record each time the wearer touches his or her face as well as when patient visits a hot zone identified by the smart-search engine; 6) this smart mask can pair with other devices like pulse oximeter to fine tune diagnosis; 7) a test interface to guide the user with some simple exercise to improve diagnosis. For instance, the instruction could include deep breathing and holding breath, then the mask can measure lung capacity via inhale and ability to hold breath without coughing.

Using AI, and based on patterns of coughing, body temperature, nausea, and shortage of breath, all measurable using the smart face mask as well as the locations the user has visited using geo-tracking and smart search-engine, the risk of coronavirus and its severity is estimated. Using a smart phone or smart watch, the data is shared through a HIPAA compliant server accessible to care providers with the permission of the users. Users could receive alerts if their symptoms need to be reviewed by a qualified care providers and qualified care providers could review symptoms and provide personalized recommendations including the need to self isolate or the need visit a medical facility. Employing geo-tracking using the user's smart phone or smart watch, a dedicated geo-tracking chip, or a fitness tracker that includes geo-tracking capabilities tracks the area that the user has visited and shares this information with care providers in case the symptoms are diagnosed as possibly COVID-19. The area visited by patients will be mapped with areas with hot zones of risk of COVID-19 infection through the smart search-engine to further fine tune the risk of infection. A particular feature and advantage of the "Smart Mask" device of the present disclosure is its ability to keep healthy people safe and facilitate patients' access to qualified clinicians and reliable health information while avoiding crowded hospitals or public transit, while giving people peace of mind for timely intervention.

Also, while PCR based test kits may still not be available to everyone in need, a simple questionnaire together with accessible wearable sensors are able to provide raw data for COVID-19 basic screening. Because 70-80% of COVID-19 cases are expected to be mild or moderate, it is important to provide a home based monitoring and tracking mechanisms so that patients do not overload local medical resources. At the same time, it also is crucial to provide such mechanisms to alert patients when they progress to potentially severe conditions. Thus, the present disclosure in a preferred embodiment also includes a questionnaire which can be uploaded to the user's smart phone. The questionnaire can report user health information such as tiredness (e.g. a bar showing up on mobile phone or smart watch which the user can slide to indicate the level of tiredness), sore throat, aches and pains, headaches, stomach upset, hours or days of symptoms, travel history, age, gender, prior chronic diseases, known contact with sick individuals or crowded venues, and other information. The questionnaire also may guide the user through certain tests such as to suggest that the user "take a deep breath and hold for 10 second"; the mobile phone or smart watch would then beep or display dots/spinning wheel for 10 seconds. Then, the questionnaire asks if the user feels chest tightness, discomfort, and experiences coughs. If the user successfully finishes this procedure, the likely conclusion is that user does not have pulmonary fibrosis which is an indication of serious infection in the lungs. Natural Language process technology can be applied to facilitate oral input for the questionnaire.

The smart mask of the present disclosure also may detect body temperature, respiratory activity and oxygen level to assess whether the user has a fever, shortness of breath, and the level of hypoxemia. The smart mask also may have a built-in temperature sensor for recording body/core temperature, MEMS based accelerometers, pressure sensors or sound sensors, e.g., microphones, for recording respiratory activities, and oxygen sensors for recording $PO_2$ and/or $SPO_2$ levels. The temperature sensor and $SPO_2$ sensor preferably are located at top end sides of the mask mesh so that they can be adhered or pressed to the users' temple. The $PO_2$ sensor, the pressure or sound sensor and accelerometer preferably are located adjacent the center of the mask. The mask also preferably is formed of an appropriate material to form a triboelectric generator as air flows through the mask. For example, the smart mask may be formed of an electrospun nanofiber mesh, which may be formed integrally with the face mask, or worn outside a regular face mask, surgical mask, or N95/N99 masks. The smart mask also may include copper or silver or copper alloys or graphene based materials (or other metals and metal alloys) based mesh to reduce the possibility of virus surviving on the surface of the mask. A triboelectric generator can produce two opposite electrical fields to establish electrostatic absorption or repellant. When used as electrostatic absorption mode, the smart mask can absorb COVID-19 virus (which has a particle size of about 100 nm) so the infected user who wears mask would have less transmission possibility. When used as electrostatic repellant mode, the smart mask can repel COVID-19 virus so the user can better protect him/herself. With the enhanced electrostatic mask, it is expected that we can remove 90% percent of 100 nm particles (e.g. COVID-19 virus). Mask mesh size could be made smaller or larger to capture/block smaller size particles as in the case of other viruses or other pathogens, molds, etc.

Another feature and advantage of the smart mask of the present disclosure is use of multi-task deep learning algorithm for smart mask data processing. This deep learning algorithm can be downloaded from the cloud to a user's mobile phone platform, with pre-activated ResBlocks and Long-Short Term Memory (LSTM). The learning architecture preferably also includes convolutional neural networks (CNNs), recurrent neural networks (RNNs), and fully connected neural networks (FCNNs). Questionnaire acquired user information and daily measurements from wearable sensors constitute inputs to the system architecture. ResBlocks and Long-Short Term Memory (LSTM) can extract, store and correlate signal features from smart mask sensors and questionnaire information. Also optionally included in the smart mask system are user data inputs for other data such as chest CT scans. Both $PO_2$ and chest CT scans have been used in COVID-19 detection and screening in other epicenter countries when PCR based test kits are not available. The output of this learning architecture is the probability of infection. If users have a possibility to get infected, the disclosed method has the ability to also score users temporarily as mild, moderate, and potential severe. The user data inputs may be supplemented with available current/historical database with existing reported cases from various publications, questionnaire interface and basic multi-tasking learning architecture for this task.

BRIEF DESCRIPTION OF THE DRAWINGS

Further features and advantages of the present disclosure will be seen from the following detailed description take in conjunction with the accompanying drawings, wherein like numerals depict like parts, and wherein:

FIG. 5 illustrates a face mask having copper mesh layers on the inside and outside of a conventional mask material;

FIG. 6 schematically illustrates a triboelectric generator formed from two copper mask layers in accordance with the present disclosure.

DETAILED DESCRIPTION OF THE DISCLOSURE

Figure 1:
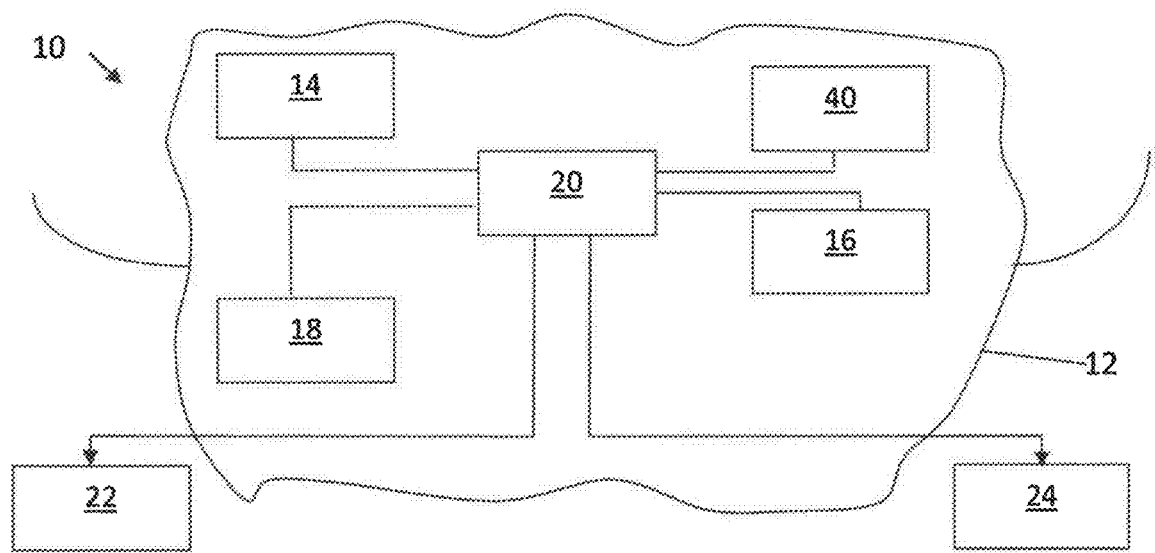
FIG. 1 is a plan view of a face mask in accordance with one embodiment of the present disclosure.

Referring to FIG. 1, a face mask 10 in accordance with the present disclosure includes a mask body 12 having a temperature sensor 14 in the form of a digital thermometer configured to contact the forehead of the wearer. Alternatively, temperature sensor 14 may be configured to measure the temperature of the expiration of the wearer. Face mask 10 also includes an expiration sensor 16 for detecting and measuring coughing, frequency of coughing, respiration rate and shortness of breath of the wearer. Sensor 16 may comprise a microphone, or a pressure or flow sensor, an accelerometer, or the like.

Face mask 10 also may include a geotracking chip 18, which includes both a geotracking capability and optionally a time clock. Alternatively, the user's smart watch or smart phone may provide this information. Temperature sensor 14, expiration sensor 16 and geotracking chip 18 are tied together by a communications chip 20 which collects and transmits output data to a smart phone 22 or smart watch 24 worn by the wearer, which smart phone or smart watch in turn communicates this data to a central processor as discussed below, via the cloud.

Figure 2:
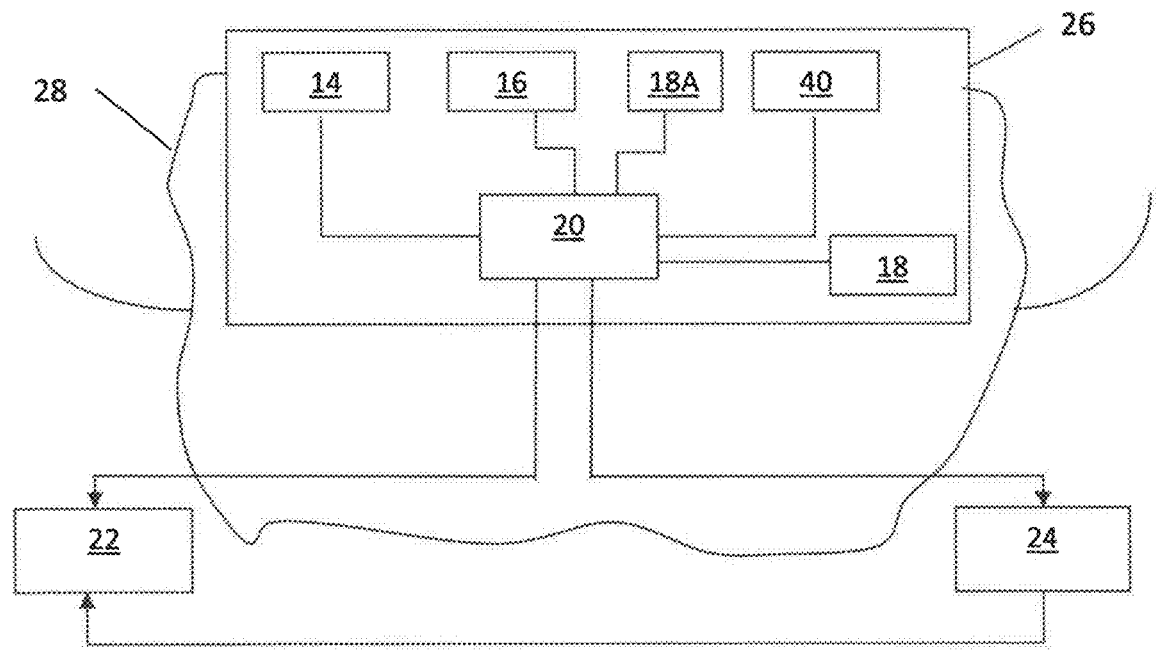
FIG. 2 is an exploded view of a second embodiment of a face mask in accordance with the present disclosure.

Alternatively, as shown in FIG. 2, the temperature sensor 14, expiration sensor 16, and geotracking chip 18A may be fitted to a separate add-on strip 26 which may be affixed to the inside surface of a conventional face mask 28.

Also, in another embodiment, the geotracking information could be received from a separate commercially available geotracking fitness device such as a FitBit™ tracker.

Figure 3:
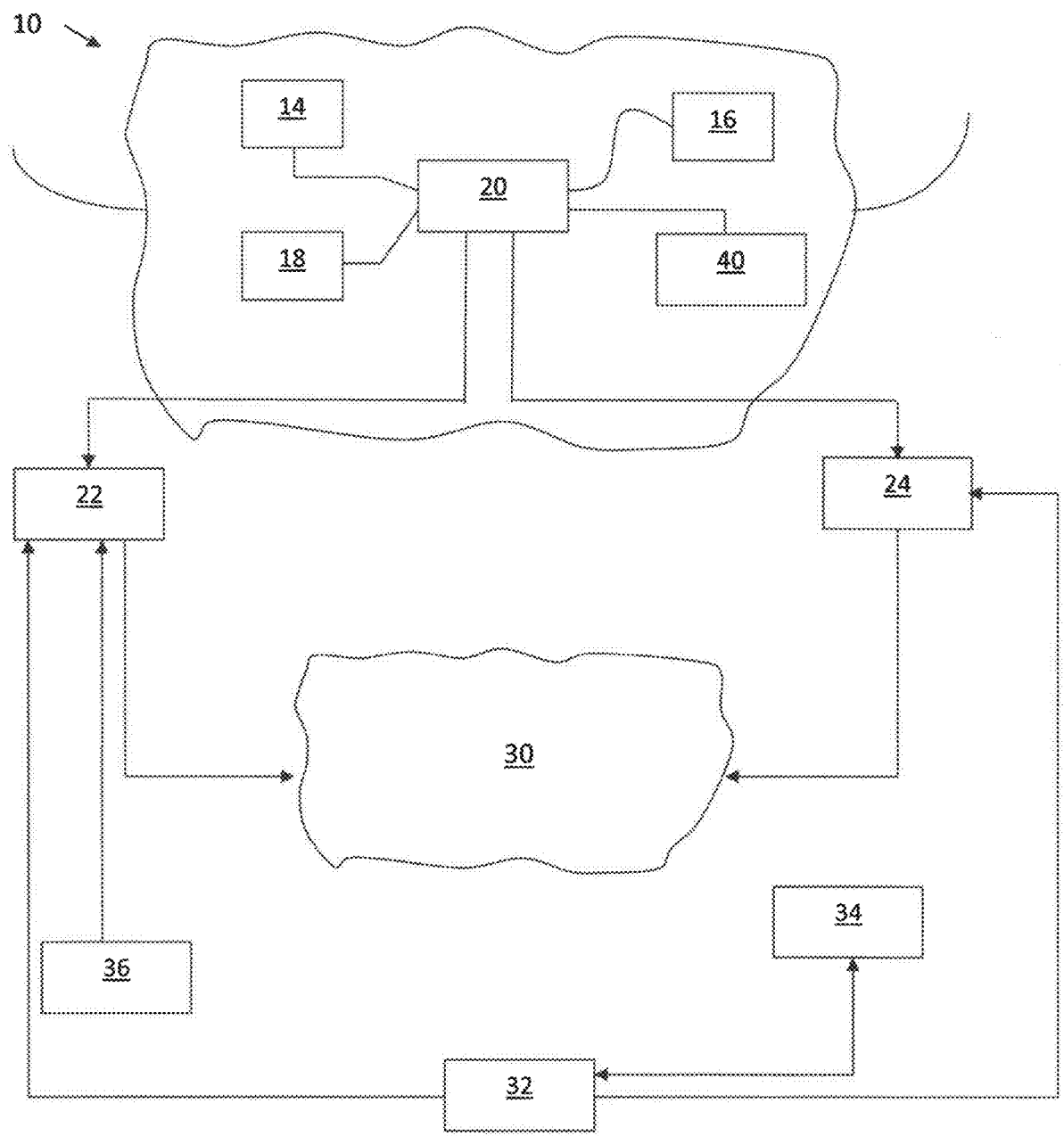
FIG. 3 is a schematic diagram of a screening, tracking and monitoring process of the present disclosure.
Figure 4:
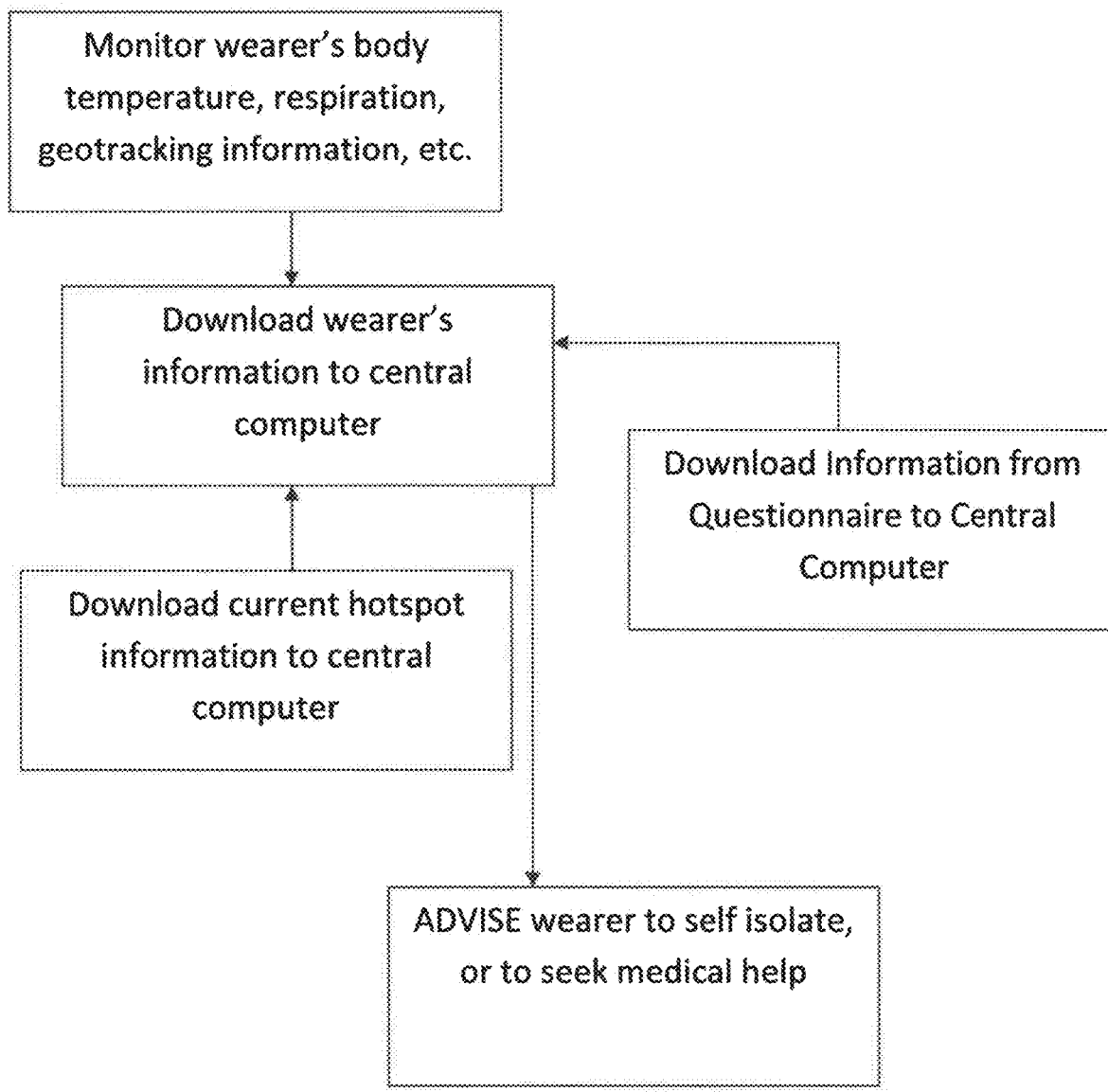
FIG. 4 is a flowchart representation of a process of the present disclosure.

Referring to FIGS. 3 and 4, in implementation, a user activates and dons a mask 10. The mask connects to the wearer's smart phone 22 or smart watch 24, and begins transmitting temperature, expiration and geopositioning information to the smart phone or smart watch, which in turn transmits the information to the cloud 30 where the information is shared through a HIPAA compliant server 32 accessible to healthcare providers 34. Temperature, expiration and geopositioning information may be streamed continuously, or to conserve battery life, intermittently.

A system may include a camera 40 and a computer readable memory configured to store prerecorded images of a human hand, whereby the processor may determine when the wearer's hand is brought close to the camera, by comparing the images detected by the camera with the image information of a hand stored in the computer readable memory.

Also, in a preferred embodiment, the user may input certain health information in response to a questionnaire 36 which is uploaded to the user's smart phone, on activation of the mask. This information might include one or more of the following health data points including but not limited to tiredness, sore throat, headaches, stomach upset, aches and pains, hours or days of symptoms, travel history, age, gender, existing chronic diseases, known contact with sick individuals, and other basic information.

The information received from the smart phone or smart watch is then processed by the HIPAA compliant server 32 and conveyed to healthcare providers 34. Upon determination that the user may be getting sick or is sick, a message is sent to the user's smart phone 22 or smart watch 24 with instructions to take precautions to self isolate, or to visit the nearest, or a specific health care facility, as the case may be. Thus, unnecessary trips to crowded medical facilities may be avoided.

Various changes may be made in the above disclosure without departing from the spirit and scope thereof. For example, referring to FIGS. 5 and 6, a smart face mask 50 in accordance with a preferred embodiment of our disclosure has a built-in electrostatic enhancement through triboelectric generator 52. A triboelectric generator is an energy harvesting device that converts external mechanical energy into electricity by a conjunction of triboelectric effect and electrostatic induction. In a triboelectric generator, a potential is created by the triboelectric effect between two thin mesh layers that exhibit opposite tribo-polarity. The triboelectric generator 52 allows the mask 50 to remove/repel COVID-19 virus of size <100 nm (negative charge). The triboelectric generator 52 comprises electrospun nanofiber mesh layers 54, 56 located on the outside/inside a regular face mask material 58. The regular face mask also can comprise a surgical mask or N95/N99 mask. The triboelectric generator produces two opposite electrical fields to establish electrostatic absorption or repellant. When used in an electrostatic absorption mode, the smart mask can absorb covid-19 virus so the infected user who wears mask would have less transmission possibility. When used as electrostatic repellant mode, the smart mask can repel covid-19 virus so the user can better protect him/herself. With the enhanced electrostatic mask, it is expected that we can remove 90% percent of 100 nm particles including COVID-19 virus.

Referring in particular to FIG. 6, copper nanofiber based mesh sheets 54, 56 are applied at the inner and outer layer of regular mask 50. Copper nanofiber mesh is available commercially from a variety of manufacturers, and typically is fabricated using electrospun nanofibrous procedures. Copper is a preferred metal because it is a metal that COVID-19 cannot survive more than four hours. Other metals or metal alloys such as silver or magnesium and graphene based materials, also may be employed. Different mask materials, e.g., paper masks, cloth masks and N95 masks, have different pore sizes. When particle size is comparable with pore size, interception and inertial impaction are the two key approaches to filter particles. Covid-19 virus (~100 nm) movement is dominated by Brownian motion, and can only be captured by the fibers through random collision. Models created by Roveda et al [1,2], Computational Fluid Dynamic (CFD) and Lagrangian simulation approach can predict the probability of virus travelling through the regular N95 or equivalent masks by 70%. The 95% of N95 as is well known only accounts for 95% filtering performance for >, 2.5 um particles (e.g. COVID-19 virus can survive on these particles) but not for direct COVID-19 virus itself.

The use of copper or other metal nanofiber mesh actively serves as proactive electrostatic enhancement to filter mask. Copper nanofiber mesh is particularly preferred due to its relatively low cost and moderate flexibility, small sheet resistance, and high transmittance. Air filters used for N95 and other face masks serve as electret plates. Electret plates for air filters follows two principles: corona charging and triboelectrification. In accordance with our disclosure, we use air filters as electret plates for vibration enhanced electrostatic property. Accordingly, we employ two layers of electrostatic fibers that have different electronegative properties as air filter materials. When these two layers rub against each other through a carding process, electrons transfer from the less electronegative fiber to the more electronegative one. Thus, when wearers move or cough or simply breathe, the copper nanofiber mesh will accumulate excessive amount of charges and thus enhance electrostatic properties of the proposed smart wearable.

Our smart mask with triboelectric generator can further be integrated with sensors as described previously, e.g., air pressure and flow sensors, temperature sensor for body/core temperature, MEMS based accelerometers and pressure sensors for respiratory activities, and oxygen sensors for $PO_2$ and $SPO_2$ level, etc. Temperature sensors and $SPO_2$ sensors may be located at top end sides of the mask mesh that can be adhere to users' temple. $PO_2$ sensors and accelerometers may be embedded at the center of the mask mesh. The purpose of these sensors are to detect body temperature, respiratory activity, and oxygen level to assess whether the user has low fever, shortness of breath, and the level of hypoxemia.

In yet another and preferred embodiment, we employ Lagrangian Simulation for aerosol tracking and Computation Fluid Dynamics (CFD) in design of our smart masks. More particularly, we employ Lagrangian Stimulation for aerosol tracking and Computation Fluid Dynamics to optimally select mesh size, mesh pattern, distances of air filter to the copper mesh (or the height of nanowire springs) and the ability to filter COVID19 virus on aerosol. As the first step, we employ simulation based particle tracking to investigate quality of the proposed wearable design at the particle level. Then through measurements and tests in a chamber, we collect data for the smart wearable performance and then calibrate our simulation parameters. While Lagrangian simulation and CFD approaches are believed to have been developed and used in mask design considering droplets and room configurations [3-6], we believe we are the first to use a hybrid approach that combines room settings with particle level simulation (e.g. aerosols).

Initially, we examined multiple potential approaches for particle tracking simulation and decided to use the Lagrangian point particle method. These types of simulation approaches have been tested against various experiments and were shown to be able to capture the preferential concentration phenomena fairly accurately. In a typical Lagrangian simulation [7], we assume that the number of numerical particles would be equal to the number of physical particles with incompressible low speed simulation (e.g. the density of air flow remains near constant). Following these simplifications, the equation for the Lagrangian simulation are limited to particle positions Xp, and velocity Vp. Thus, we can write Lagrangian simulation as:

$$\frac{dX_p}{dt} = V_p, \text{ and} \quad (1)$$

$$\frac{dV_p}{dt} = \frac{U_g(t, X_p) - V_p}{\tau_p} \quad (2)$$

Where $\tau_p$ is the relaxation time of the particles and $U_g$ as the phase velocity of aerosol. We applied numerical methods in solving the above equations. More specifically, a 4th-order Runge-Kutta method was used to solve the Lagrangian tracking. And a 2nd order linear interpolation was used for aerosol phase disperse phase exchanges [8]. The phase equations were solved using the low-Mach number approximation [9,10]. Spatial derivatives are calculated through 2nd-order central differences. We employed iterative FFT to solve the variable coefficient Poisson equation for aerodynamic pressure to account for dilatability effects. We established computational domain as 3D computational mesh comprises hexahedral non-uniform structured cells (≈0.52× 106). The height between the top and bottom vertical planes is H=0.45 m, the length of the domain is L=1.6 m, and the width is W=0.5 m. FIG. 6 shows a close-up grid around the face. Note that with different layers of our smart face mask, we need to refine the mesh near the mouth, face, and the nose with different initial boundary conditions. Using a multi-level mesh technique and the grid convergence index (GCI) [11], we investigated a mesh convergence for the flow variables (aerosol velocity and pressure).

Figure 7:
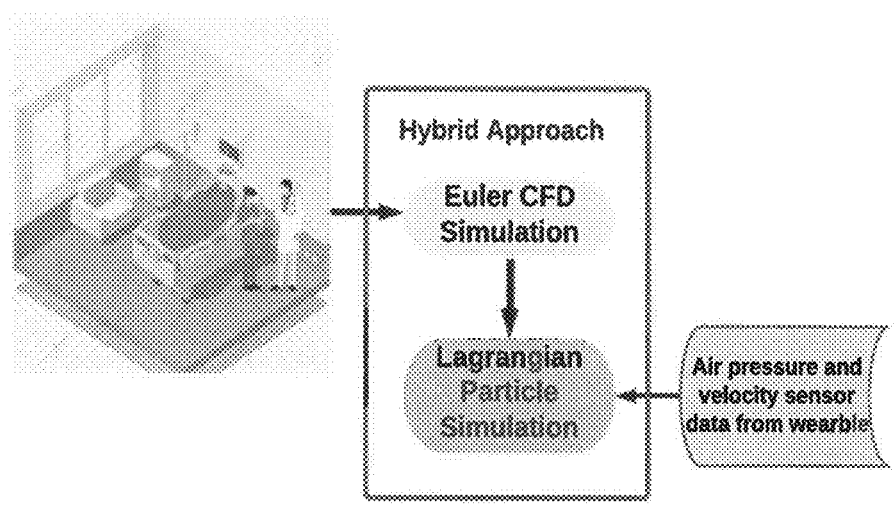
FIG. 7 schematically illustrates a hybrid method with Euler based CFD distribution for a room setting and then passes boundary condition to Lagrangian particle stimulations in accordance with the present disclosure.

Through the above study, we were able to understand how we can enhance face mask protection. However, we assumed that we are in a static environment with ideal setting. In general, we expected that the proposed smart mask will be used in a room with potential contamination. Therefore, Lagrangian particle tracking simulation by itself is not enough to capture the aerodynamics of aerosols inside a room. Thus, we used hybrid method. [1,2,12-16]. The idea was to use Euler based computational fluid dynamics (CFD) model to investigate air flow inside the room and then update boundary conditions for grids (refer to FIG. 6 right hand side) for smart wearable mask Lagrangian tracking. FIG. 7 demonstrates our hybrid method starting with Euler based CFD simulation for a room setting and then passing to boundary conditions to Lagrangian Particle Simulation. Air pressure and velocity sensors on the proposed wearable mask provide measurement data to Lagrangian simulations for the localized pressure and velocity parameters.

Consider a room in a hospital setting with supply of air flow and exhaust. The diffusion of contamination inside the room can be analyzed according to the type and location of air supply and exhaust. To illustrate, we used Euler simulation for the dynamics of the ventilation flow and the airborne contamination by a patient's cough. First, we computed the steady-state ventilation flows until we reach convergence. Then we used a time-accurate Euler algorithm to obtain the contamination diffusion seconds after a cough [17]. We assumed 250 $m^3$/hr as the constant flow rate for air supply from the inlet flow with an air-changing rate of 10 ACH. We also assumed an exhaust of the ventilation system at a constant outflow rate to maintain −8 Pa negative pressure. We modeled cough as a transient flow with rate as a skewed triangular pulse with the duration of seconds (whole coughing process)[17]. By using air flow and pressure sensors, we obtained cough characteristics. If we assume a patient infected with COVID-19 virus, the main source of contamination is the mouth of the patient with the mole fraction of 0.02 using the scalar transport equation. FIG. 7 displays the room setting with air inlet and exhaust. It also demonstrates the CFD computation results of air flow inside one room. Using ANSYS-FLUENTF software [18] with different velocity profiles by introducing two user-defined functions (UDFs), the input vertical velocity profiles are presented, and the results compared with air flow sensors and pressure sensors on smart wearables to refine boundary conditions.

Still other changes may be made in the above disclosure without departing from the spirit and scope thereof.

The invention claimed is:

1. A telehealth platform, comprising:
a HIPAA compliant server accessible to healthcare providers;
a smart face mask having a paper or cloth mask body wherein inside and outside surfaces of the mask body are covered, at least in part, with metal nanofiber mesh sheets configured to form a triboelectric generator, the smart face mask further comprising a temperature sensor, a respiration sensor, an $SpO_2$ sensor, and a transmitter configured for transmitting information from the temperature sensor and the respiration sensor to a smart phone or smart watch;
a test interface configured to guide a wearer with a breathing exercise to measure lung capacity; and
the smart phone or smart watch, configured to receive said information from the smart mask and to transmit said information to the HIPAA compliant server accessible to healthcare providers, wherein said HIPAA compliant server is configured to transmit a message to the smart phone or smart watch in the event the information transmitted to the HIPAA compliant server is indicative that the wearer of the smart mask may be getting sick or is sick.

2. The telehealth platform of claim 1, wherein the temperature sensor comprises a digital thermometer and is configured to measure body temperature via the skin of the wearer or via contact with respiratory expiration of the wearer.

3. The telehealth platform of claim 1, wherein the respiration sensor comprises a pressure or flow sensor configured to measure an expiration flow or frequency of breathing from the nose or mouth of the wearer, or changes in expiration flow or frequency of breathing from the nose and/or mouth of the wearer.

4. The telehealth platform of claim 1, wherein the respiration sensor comprises a microphone configured to record respiration sounds from the wearer, and the HIPAA compliant server is configured to determine labored breathing or changes in respiration of the wearer.

5. The telehealth platform of claim 1, wherein the mask also includes a camera.

6. The telehealth platform of claim 1, wherein the respiration sensor comprises an oxygen or carbon dioxide gas sensor.

7. The telehealth platform of claim 1, wherein the temperature sensor, the respiration sensor and a geotracker associated with the smart mask are carried on a substrate which in turn is carried on the mask body.

8. The telehealth platform of claim 1, wherein the temperature sensor, the respiration sensor and a geotracker associated with the smart mask are carried directly on the mask body.

9. The telehealth platform of claim 1, further comprising a pulse oximeter.

10. The telehealth platform of claim 1, wherein a geotracker is carried on the smart phone or smart watch.

11. The telehealth platform of claim 1, wherein the metal is selected from the group consisting of copper, silver, magnesium, and alloys thereof.

12. The telehealth platform of claim 1, wherein the mesh sheets have different mesh size configurations adjacent mouth and nose regions of the mask.

13. The telehealth platform of claim 1, wherein the smart phone or smart mask has a geotracker associated with the smart phone or smart mask.

14. The telehealth platform of claim 13, configured to receive health information selected from tiredness, sore throat, headaches, stomach upset, aches and pains, hours or days of symptoms, travel history, age, gender, existing chronic disease, and known contact with individuals information.

15. The telehealth platform of claim 1, wherein the respiration sensor includes MEMS based accelerometers and pressure sensors.

16. The telehealth platform of claim 1, wherein the temperature sensor and the $SpO_2$ sensor are configured to adhere to the wearer's temple.

17. The telehealth platform of claim 1, wherein the respiration sensor is located at a center of the smart face mask.

18. A method for remote triage monitoring of individuals, comprising providing a telehealth platform as claimed in claim 1, monitoring individuals wearing the smart mask, and instructing monitored individuals to self isolate or to seek medical help based on the monitoring.

19. The method of claim 18, further comprising inputting personal health information to the telehealth platform.

* * * * *